United States Patent [19]

Bihl et al.

[11] 4,355,635
[45] Oct. 26, 1982

[54] ADJUSTABLE ARM SLING WITH POUCH

[75] Inventors: Claudia J. Bihl, Franklin Furnace; Michael C. Molloy, Cincinnati, both of Ohio

[73] Assignee: Jung Products, Inc., Cincinnati, Ohio

[21] Appl. No.: 167,772

[22] Filed: Jul. 14, 1980

[51] Int. Cl.³ .............................................. A61F 5/40
[52] U.S. Cl. ................................ 128/94; 128/DIG. 15
[58] Field of Search ................. 128/94, 95, 78, 77, 128/DIG. 15

[56] References Cited

U.S. PATENT DOCUMENTS

| 114,615 | 5/1871 | Smitley . | |
|---|---|---|---|
| 339,160 | 4/1886 | Galt . | |
| 740,712 | 10/1903 | Tabler . | |
| 803,286 | 10/1905 | Hingston . | |
| 980,464 | 1/1911 | Wermuth | 128/94 |
| 1,267,142 | 5/1918 | Stowers et al. . | |
| 1,304,153 | 5/1919 | Bugge . | |
| 1,490,381 | 4/1924 | Gobar . | |
| 1,621,323 | 3/1927 | Horn . | |
| 2,111,963 | 3/1938 | Coombs . | |
| 2,652,050 | 9/1953 | Schoeller | 128/94 |
| 2,796,862 | 6/1957 | Borntraeger . | |
| 2,856,919 | 10/1958 | Murray . | |
| 3,103,216 | 9/1963 | Scott . | |
| 3,108,589 | 10/1963 | Staggs | 128/94 |
| 3,307,538 | 3/1967 | Groll | 128/94 |
| 3,404,680 | 10/1968 | Gutman et al. . | |
| 3,515,131 | 6/1970 | Stevens . | |
| 3,554,194 | 1/1971 | Johnson | 128/94 |
| 3,706,310 | 12/1972 | Garnett | 128/94 |
| 3,780,729 | 12/1973 | Garnett | 128/94 |
| 3,815,588 | 6/1974 | Klausner . | |
| 4,071,022 | 1/1978 | Ewers | 128/94 |

Primary Examiner—Kyle L. Howell
Assistant Examiner—C. W. Shedd
Attorney, Agent, or Firm—Wood, Herron & Evans

[57] ABSTRACT

An adjustable arm sling comprising a pair of strap members each joined at one end to a ring adapted to overlie the wearer's chest, the strap members having self-adhering fastening members at their opposite ends adapted to be secured together when the straps are passed upwardly and rearwardly over the wearer's shoulders, crossed diagonally downwardly across the wearer's back, with the ends of the straps drawn around the opposite sides of the wearer's body and joined together across the front of the wearer's body by the fastening members, an arm supporting pouch, and an elongated connector tab for adjustably securing the pouch to the ring member, the connector tab comprising a cohesive fastener.

14 Claims, 6 Drawing Figures

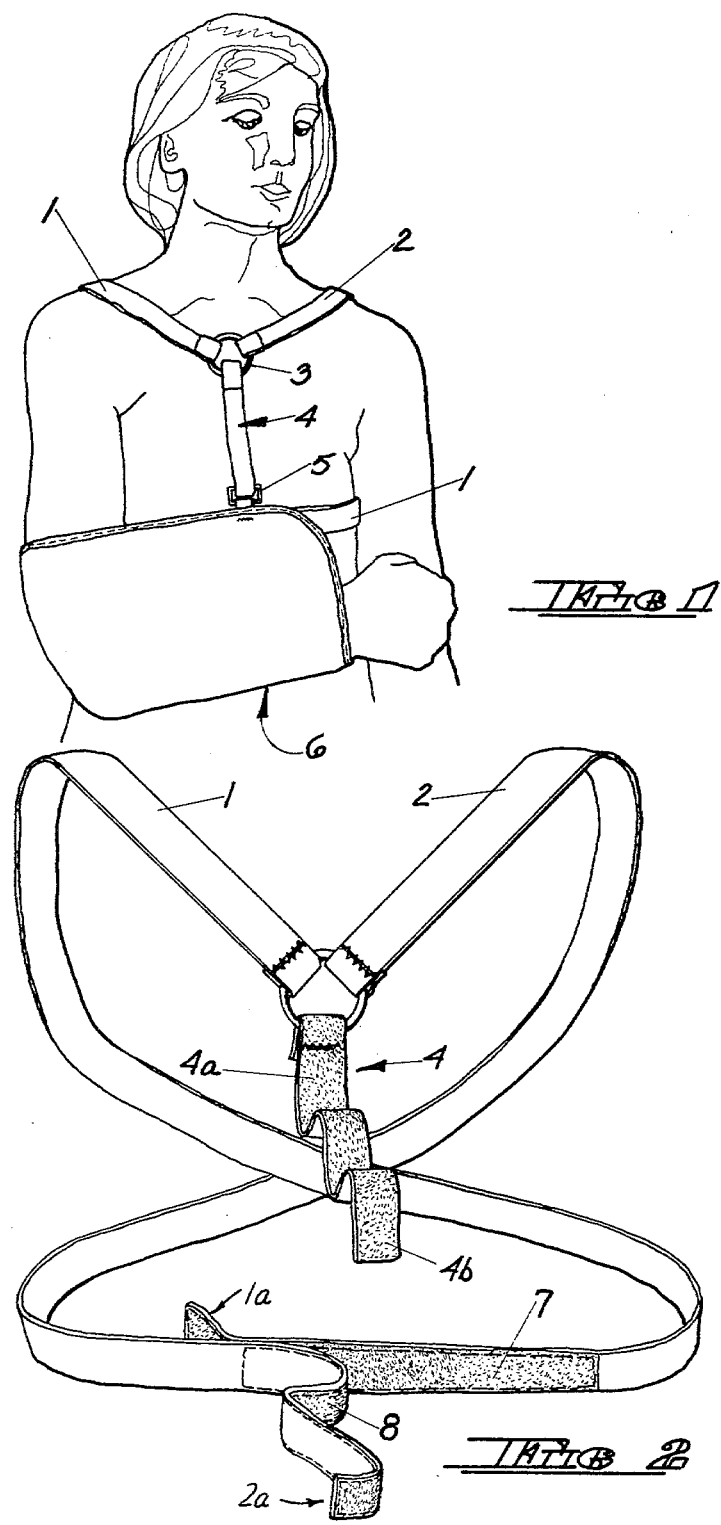

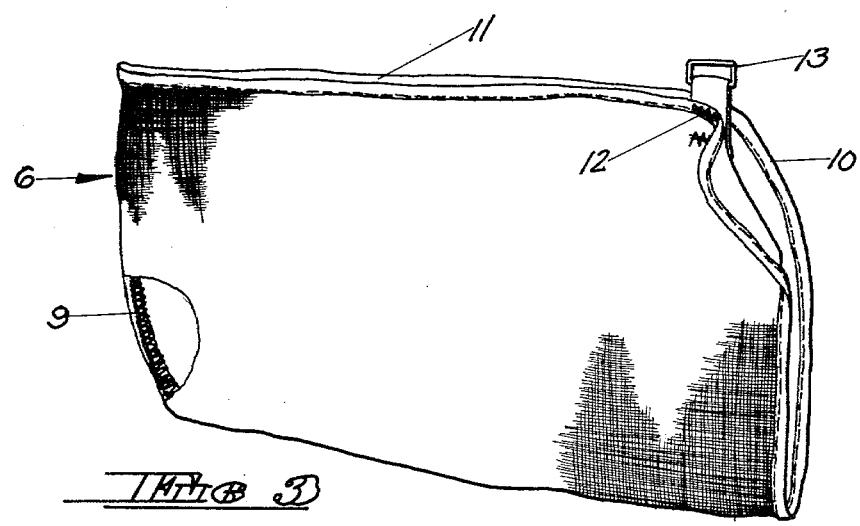
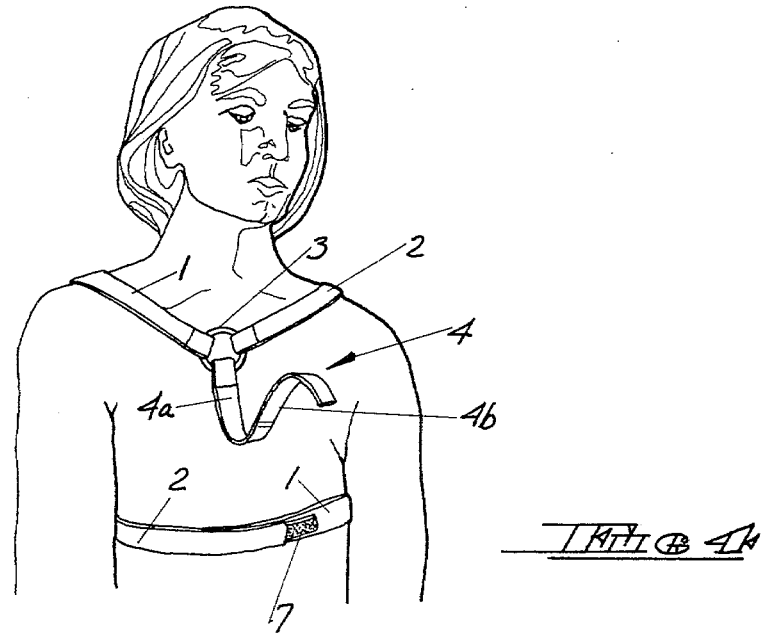

ADJUSTABLE ARM SLING WITH POUCH

This invention relates to arm slings and has to do more particularly with a pouch type sling for supporting an injured arm of the user in a comfortable position which is conducive to proper healing of the injury.

BACKGROUND OF THE INVENTION

Numerous types of arm slings have hitherto been proposed, the two most prevalent types being the neck harness and the body harness. The neck harness has the disadvantage of placing the weight load on the wearer's neck which can be uncomfortable, and while various forms of padded neck harnesses have been employed, they tend to be bulky and cumbersome. While a body harness acts to distribute the weight across the wearer's shoulders and back, the body harnesses are often cumbersome, complicated and difficult to adjust.

A major disadvantage of both types of slings is the fact that they interfere with the wearing of one's clothing in conventional fashion. This is particularly true of the body harnesses. Customarily, the slings are worn over the blouse or shirt and if the user desires to wear an outer garment, it must be draped over the wearer's shoulders.

In contrast to prior art slings, the sling of the present invention permits the user to wear clothing in conventional fashion, including a shirt or blouse, while supplying the necessary support for the injured arm.

BRIEF SUMMARY OF THE INVENTION

A sling in accordance with the present invention is of simple and inexpensive construction, comprising, in preferred form, essentially a pair of strap members each joined at one end to a metal ring adapted to overlie the wearer's chest, the ring also mounting a connector tab to which the arm supporting pouch is secured.

At their opposite ends the strap members are provided with Velcro or similar self-adhering fastening elements by means of which the straps may be joined together, the straps extending over the wearer's shoulder and crossing diagonally downwardly across the wearer's back, the ends of the straps passing around the opposite sides of the upper body and being joined together across the front of the wearer's body, thereby forming a simple weight distributing harness. The straps are preferably formed from cloth webbing which can be readily laundered.

The pouch is formed from cloth and has a closed elbow receiving end and an open opposite end through which the wearer's hand may project. The top of the pouch is essentially open so that the wearer's arm may be inserted, the opposite top edges of the pouch being secured together near the open end of the pouch and provided with a metal loop of a size to receive the connector tab attached to the metal ring. The connector tab is also in the form of a self-adhering fastener which facilitates adjustable attachment of the pouch.

In use, the strap portion of the sling may be worn adjacent the user's body or undergarments, and the user may wear a shirt or blouse in conventional fashion with only the connector tab protruding from the garment. The user's arm may then be placed in the pouch and the pouch attached to the connector tab by passing the tab through the loop on the pouch and securing together the ends of the tab. If the user desires to wear an outer garment, such as a coat, only the pouch need be removed, whereupon the coat may be put on in conventional fashion and buttoned, again with only the connector tab protruding, and the pouch reattached.

Of course, if desired, the sling may be worn over the wearer's clothing, although this is normally unnecessary.

BRIEF DESCRIPTION OF THE DRAWINGS

FIG. 1 is a partial front elevational view illustrating the sling in its normal position of use.

FIG. 2 is a front elevational view of the strap portion of the sling, including the connector tab.

FIG. 3 is a perspective view, with parts broken away, illustrating the pouch.

FIG. 4 is a front elevational view illustrating the application of the strap portions of the sling of the wearer's body.

DETAILED DESCRIPTION

Figure 5:
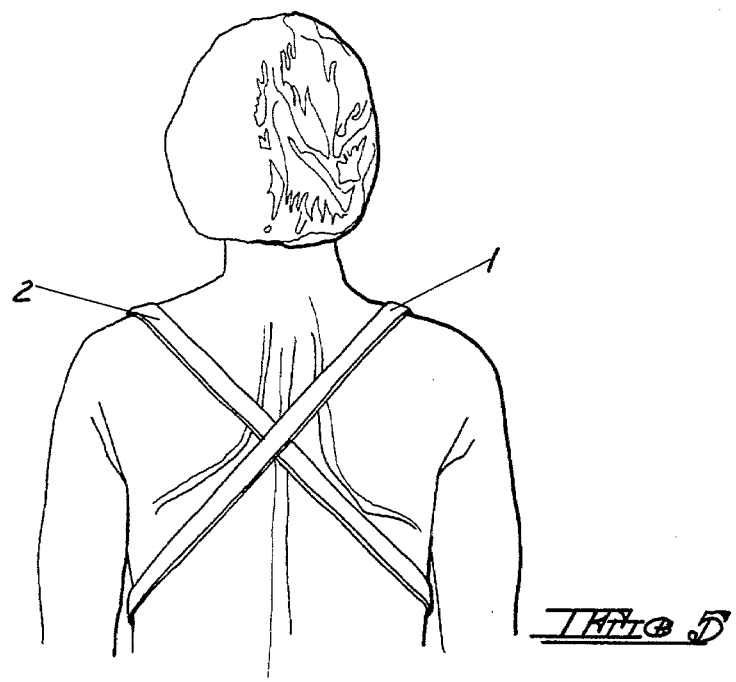
FIG. 5 is a rear elevational view similar to FIG. 4 illustrating the manner in which the strap portions of the sling cross the wearer's back.

Referring first to FIG. 1, a sling in accordance with the invention comprises a pair of elongated straps 1 and 2 secured at one end to a metal ring 3 adapted to overlie the wearer's chest, same thereby estalishing a single extended length band 1-3 having opposed ends 1a, 2a and ring 3 located on a chest area which is generally midway between the band's ends. A connector tab 4 is also secured to the ring 3 and depends therefrom, the tab engaging a metal loop 5 secured to the cloth pouch 6, the connector tab and metal loop constituting a connector by which the pouch is connected to the band 1-3.

As seen in FIG. 2, the pile portion 7 of a self-adhering or cohesive fastener, such as a Velcro type fastener, is secured to the outer surface of strap 1 towards its free end, and the coacting portion 8 of the fastener, which is in the form of minute hook-like projections, is secured to the inner surface of strap 2. Preferably, the length of the fastener portions 7 and 8 will be approximately 12 inches, and the length of the straps 1 and 2 will be approximately 36 inches, thereby allowing for essentially infinite adjustment to different body widths and proportions. Of course, if desired, the sling may be produced in different sizes for use by adults or children.

The connector tab 4 is also in the form of a self-adhering or cohesive fastener, the tab having a pile portion 4a adjacent the ring 3 and a coacting portion 4b, the two portions being of essentially the same length, which may be approximately 4 inches each.

Referring next to FIG. 3, the pouch 6 is formed of cloth and has a stitched closed end 9, an opposing open end 10, and an open top 11 except that adjacent the open end 10 the top of the pouch is closed for a short distance by a line of stitching 12 which also secures a short length of webbing 13 which fastens the metal loop 5 to the pouch.

In use, the wearer applys the sling by positioning the metal ring 3 centrally over the chest with the straps 1 and 2 extending rearwardly over each shoulder. The straps are then crossed over the wearer's back, as seen in FIG. 5, whereupon the strap 1 is brought around one side of the wearer's upper body and across the front of the body, the strap 2 being brought around the opposite side of the wearer's body and the straps juxtaposed with the coating portion 8 of the fastener juxtaposed and joined to the pile portion 7, the strap thus assuming the position illustrated in FIGS. 2 and 4, which position is in the nature of a closed loop that can be described as a figure 8 loop. As should be evident, the mode of attachment of the straps of the wearer's body is the same irrespective of whether the sling is to be used to support the right or the left arm.

Figure 6:
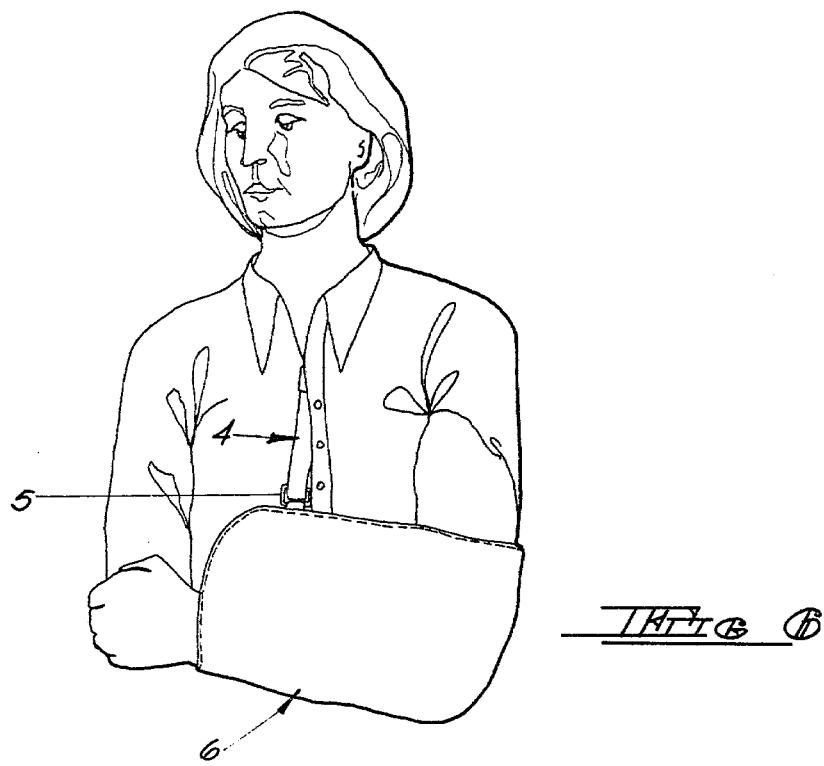
FIG. 6 is a front elevational view illustrating the manner in which the sling may be worn beneath a shirt or blouse.

Upon fitting the straps in the desired position of use (which position is comfortable against the user's chest since ring ends of the strap 1, 2 slide on metal ring 3, thereby permitting the straps to the lie flat against the user's chest as shown in FIGS. 1 and 4), the wearer may then put on a shirt or blouse in essentially conventional fashion with only the connector tab 4 projecting outwardly from beneath the garment. The user then fits the pouch 6 on the injured arm, the hand and arm being inserted inwardly through the open top 11 with the hand projecting outwardly through the open end 10, the elbow thus seating at the closed end 9 of the pouch. The connector tab is then engaged through the metal loop 5 of the pouch and the fastener portions 4a and 4b juxtaposed and secured together. The position of the pouch may be adjusted depending upon the location at which the fastener portions 4a and 4b are joined together. As will be evident from FIG. 6, the strap portion of the sling may be worn beneath a shirt or blouse, or other outer garment, with only the connector tab protruding for engagement with the pouch. This greatly simplifies the use of the sling and provides enhanced comfort for the wearer.

As should now be evident, the present invention provides a simple yet highly effective sling which may be readily adjusted to suit the needs of the wearer. The use of self-adhering or cohesive fasteners for both strap closing and for the connector tab provides a broad range of adjustment for fitting, as well as for comfort and the ability to easily adjust the pouch to another comfortable position.

What is claimed is:

1. An adjustable arm sling consisting essentially of:
   (a) a ring member adapted to be centrally disposed one the wearer's chest,
   (b) a pair of elongated strap members each secured at one end to said ring member, said strap members being of a length to pass upwardly and rearwardly over the wearer's shoulders and cross diagonally downwardly across the wearer's back, the strap members passing around the opposite sides of the wearer's upper body and meeting across the front of wearer's upper body, said ring and said strap members thereby establishing a figure 8 loop configuration over the shoulders and around the torso of the wearer when said sling is worn,
   (c) fastening means on the ends of said strap members for adjustably joining together their meeting ends,
   (d) an arm supporting pouch, and
   (e) an elongated connector tab for adjustably securing said pouch to said ring member.

2. The adjustable arm sling claimed in claim 1 wherein said connector tab is foldable upon itself and includes fastening means for joining together the folded portions of the tab.

3. The adjustable arm sling claimed in claim 2 wherein said fastening means comprises a cohesive type fastener, the pile portion of the fastener comprising one end of the connector tab and the coating portion comprising the other end of the connector tab.

4. The adjustable arm sling claimed in claim 3 wherein said arm pouch includes a loop, and wherein said connector tab is engaged with said loop.

5. The adjustable arm sling claimed in claim 1 wherein the fastening means on the ends of said strap members comprise a cohesive fastener having a pile portion secured to one of the straps and a coating portion having minute hook-like projections secured to the other of said straps.

6. The adjustable arm sling claimed in claim 5 wherein said connector tab also comprises cohesive fastener having a pile portion and a coating portion having minute hook-like projections, said connector tab being foldable upon itself with the pile forming portion of the fastener comprising one end of the connector tab and the coating portion comprising the other end of the connector tab.

7. An arm sling comprising
   an extended length band comprising a ring member and a pair of strap members, each of said strap members being secured at one end to said ring member, said band having opposed ends and a chest engaging area positioned therebetween, said ring member being located in said band's chest engaging area, said band being of a length to pass upwardly and rearwardly over the wearer's shoulders, to thereafter cross diagonally downwardly across the wearer's back, and to thereafter pass around opposite sides of a user's upper body until said band's opposed ends meet, when said band's chest area is positioned against the user's chest, thereby providing said extended length band in a generally figure 8 loop configuration over the chest, over the shoulders and around the torso of the user when said sling is being worn,
   fasteners on said band's opposed ends for joining together said opposed ends in said figure 8 loop configuration,
   an arm support, and
   a connector means for connecting said arm support to said band at a position located generally at said band's chest area, said connector means being attached to said ring and being connectable to said arm support.

8. An arm sling as set forth in claim 7, said strap members being slidable on said ring for allowing said strap members to lie comfortably flat against the user's chest when said sling is being worn.

9. An arm sling as set forth in claim 7, said fasteners being adjustable to permit said extended length band to be used by plural users with different size upper bodies.

10. An arm sling as set forth in claim 9, said fasteners comprising
    a cohesive fastener having a hook portion secured to one end of said band and a loop portion secured to the other end of said band.

11. An arm sling as set forth in claim 7, said connector being adjustable to permit said arm support to be raised or lowered relative to said ring as desired by the user.

12. An arm sling as set forth in claim 11, said connector means comprising
    a connector tab attached at one end to said ring, said connector tab being foldable upon itself, and
    fastening means for joining together the folded portions of the tab.

13. An arm sling as set forth in claim 12, said fastening means comprising a cohesive fastener having a hook portion secured to one end of said connector tab and a loop portion secured to the other end of said connector tab.

14. An arm sling as set forth in claim 7, said arm support comprising an arm supporting pouch, that portion of said connector connected to said pouch being connected to said pouch adjacent to the user's wrist when the user's arm is in said pouch and said sling is being worn.

* * * * *